United States Patent [19]

Bales et al.

[11] Patent Number: 5,208,299

[45] Date of Patent: May 4, 1993

[54] NONLINEAR OPTICAL ARYLHYDRAZONES AND NONLINEAR OPTICAL POLYMERS THEREOF

[75] Inventors: Stephen E. Bales; David J. Brennan; Robert J. Gulotty; Anthony P. Haag; Muthiah N. Inbasekaran, all of Midland, Mich.

[73] Assignee: The Dow Chemical Company, Midland, Mich.

[21] Appl. No.: 866,400

[22] Filed: Apr. 10, 1992

[51] Int. Cl.$^5$ .................. C08F 20/00; C08G 8/02; C08G 63/00

[52] U.S. Cl. .................. 525/437; 528/125; 528/176; 528/203; 528/210; 525/376; 525/377; 564/250; 564/251

[58] Field of Search .......... 564/250, 251; 525/437, 525/376, 377; 528/176, 203, 210, 125

[56] References Cited

U.S. PATENT DOCUMENTS

| | | | |
|---|---|---|---|
| 4,247,477 | 1/1981 | Gruber et al. | 564/251 |
| 4,468,494 | 8/1984 | Barton et al. | 525/353 |
| 4,621,156 | 11/1986 | Barton et al. | 564/250 |
| 4,732,904 | 3/1988 | Morgan | 546/300 |
| 4,867,540 | 9/1989 | DeMartino | 350/355 |
| 4,909,608 | 3/1990 | Frazier, III | 350/354 |

FOREIGN PATENT DOCUMENTS 0099552 7/1983 European Pat. Off. .
62-210431 3/1986 Japan .

OTHER PUBLICATIONS

Abstract J6 3275-553-A, Pub. Date: Nov. 14, 1988, Application No: JP-110,646 Title: New organic nonlinear optical compounds Applicant: Nippon Teleg & Teleph.

*Primary Examiner*—John Kight, III
*Assistant Examiner*—T. Mosley

[57] ABSTRACT

The present invention relates to nonlinear optical material comprising nonlinear optical dihydroxy arylhydrazones and to nonlinear optical materials comprising compositions containing at least one divalent moiety of nonlinear optical arylhydrazones. The present invention also relates to polyesters, polyestercarbonates, polycarbonates, polyethers, and poly(hydroxy ether) polymers, incorporating the dihydroxy arylhydrazone as recurring divalent moieties in the backbone of the polymer. The polymeric compositions of the present invention have high glass transition temperatures and exhibit stable nonlinear optical activity at high temperatures over a period of time.

50 Claims, No Drawings

NONLINEAR OPTICAL ARYLHYDRAZONES AND NONLINEAR OPTICAL POLYMERS THEREOF

FIELD OF THE INVENTION

The present invention relates to dihydroxy arylhydrazones exhibiting nonlinear optical properties, and to materials comprising divalent moieties derived from nonlinear optical dihydroxy arylhydrazones. More particularly the present invention relates to novel nonlinear optical (NLO) polymeric compositions containing divalent moieties derived from the dihydroxy arylhydrazone in the backbone of the polymers and exhibiting stable nonlinear optical activity.

BACKGROUND OF THE INVENTION

Information may be more rapidly processed and transmitted using optical as opposed to electrical signals. Optical signals can be used to enhance the performance of electronics processors. For example, electronic wires interconnecting integrated circuits (ICs) can be replaced with optical interconnects and the information processed with IC driven electro-optic modulators. Optical signals in fiber optic communications can be encoded on the optical carrier using electro-optic (EO) modulators. In both of these processes, nonlinear optical materials with second-order nonlinear optical activity are necessary to effect modulation of the light signal.

Nonlinear optical materials can also be used for frequency conversion of laser light. Such a conversion is desirable in many applications. For example, optical memory media are presently read using 830 nm light from diode lasers. The 830 nm light wavelength limits the spot sizes which can be read and hence the density of data stored on the optical memory media. Similarly, in fiber optic communications, light wavelengths of 1.3 $\mu$m or 1.5 $\mu$m are desirable due to the low transmission losses of glass fiber at those wavelengths. However, those wavelengths are too long for detection by Si based detectors. It is desirable to frequency double the 1.3 $\mu$m or 1.5 pm wavelengths to 650 nm or 750 nm wavelengths where Si based detectors could be used.

Nonlinear optical materials which have been used in electro-optic devices have in general been inorganic single crystals such as lithium niobate (LiNbO$_3$) or potassium dihydrogen phosphate (KDP). More recently, nonlinear optical materials based on organic molecules, and in particular polar aromatic organic molecules have been developed.

Organic nonlinear optical materials have a number of potential advantages over inorganic materials. First, organic nonlinear optical materials have higher NLO activity on a molecular basis. Organic crystals of 2-methyl-4-nitroaniline have been shown to have a higher nonlinear optical activity than that of LiNbO$_3$. Second, the nonlinear optical activity of the organic materials is related to the polarization of the electronic states of the organic molecules, offering the potential of very fast switching times in EO devices. The time response of the organic nonlinear optical system to a light field is on the order of 10 to 100 femtoseconds. In contrast, a large fraction of the second order polarizability in the inorganic crystals in EO applications is due to nuclear motions of the ions in the crystal lattice, slowing the time-response of the materials. In addition, the low dielectric constant of the organic materials (e.g., 2-5 Debye at 1 MHz) compared to the inorganic materials (e.g. 30 Debye at 1 MHz) enables higher EO modulator frequencies to be achieved for a given power consumption. Third, the organic materials can be easily fabricated into integrated device structures when used in polymer form.

EP 218,938 and U.S. No. 4,859,876 have used an approach of incorporating NLO active molecules into amorphous polymer host matrices for NLO media. The NLO molecules are incorporated into the host by blending. Such doped polymers have the advantages of being easily fabricated into thin films suitable for integrated optical devices. The media contain organic molecules (dopants) with nonlinear optical activity with the advantages discussed above. These films must be oriented to achieve a non-centrosymmetric alignment of the NLO ohromophores. Such alignment is usually achieved by the application of an electric field across the film thickness while the temperature of the polymeric blend is above or near its glass transition temperature (Tg). The polymer is then cooled with the field on to lock the oriented molecules in place. EP 218,938 discloses a number of polymer host materials, including epoxies, and many types of molecules which have NLO activity including azo dyes such as Disperse Red 1. It is known that an NLO active material such as azo dye Disperse Red 1, (4-[N-ethyl-N-(2-hydroxyethyl]amino-4-nitro azobenzene), may be incorporated into a host by simply blending the azo dye in a thermoplastic material such as poly(methylmethacrylate), as described in Applied Physics Letters 49(5), 4 (1986) and U.S. Pat. No. 4,859,876.

While the doped polymer approach offers some advantages over organic and inorganic crystals, the approach has a number of problems. First, the stability of the NLO activity over time of such materials has been shown to be poor. A problem associated with a polymer with NLO properties produced by simply blending NLO molecules into a host polymer is that these polymer materials lack orientational stability. There is significant molecular relaxation or reorientation within a short period of time resulting in a loss of NLO properties. For example, as reported by Hampsch et al., Macromolecules 1988, 21, 528–350, the NLO activity of a polymer with NLO molecules blended therein decreases dramatically over a period of days at room temperature.

In addition, the NLO dopants in the blended polymeric media plasticize the polymer host matrix, lowering the polymer glass transition temperature (Tg). Lowering the polymer Tg has the effect of lowering the temperature stability of the electrically oriented NLO material or NLO medium. Near the Tg, segments of the polymer become mobile and the NLO active dopant molecules which were oriented electrically undergo orientational relaxation. Once orientational relaxation has occurred, the NLO medium exhibits no NLO activity.

A third problem with the doped polymers is the poor solubility of the NLO chromophore in the host matrix. Finally, the NLO chromophores tend to aggregate at relatively low doping levels (e.g., 5–20 percent w/v). Such aggregates scatter light and reduce the transparency of the waveguides to unacceptable levels.

Another disadvantage is that the polymer employed may have a low glass transition temperature, lack sufficient tensile strength, or other desirable properties for optical devices.

Japanese laid open publication Nos. J-63-275,553 and J-62-210,431 disclose various organic nonlinear optical compounds containing hydrazone functionalities which are useful for NLO applications. Specifically, J-62-210,431 discloses nonlinear optical materials containing nonlinear optical hydrazones as powders, molecule inclusions within the host lattice, thin layers deposited upon carriers such as films, monocrystals, and solutions. The hydrazones of J-62-210,431 may be bonded in the form of a pendant group to a polymer such as a polydiacetylene, but are not rigidly divalently bonded so as to form the backbone of the polymer.

It would be highly desirable to have organic polymeric materials which provide a rigid backbone comprising aryl hydrazone structural units as part of the backbone of the polymer.

It would also be desirable to provide organic polymeric materials with larger second and third order nonlinear optical properties than presently used organic electrolytic materials.

It is an object of this invention to make arylhydrazones that exhibit optical activity and are polymerizable with other commoners. It is further the object of this invention to obtain optically transparent polymers incorporating divalent moieties of the arylhydrazone structures which exhibit NLO activity upon orientation. It is an additional object of this invention that the polymers comprising the NLO materials or medium have a relatively high glass transition temperature. A high glass transition temperature will correlate with high temperature stability of the NLO material or medium.

SUMMARY OF THE INVENTION the instant invention relates to nonlinear optical materials comprising dihydroxy arylhydrazones which exhibit nonlinear optical properties. The instant invention also relates to nonlinear optical materials comprising divalent moieties derived from such dihydroxy arylhydrazones; and to polymers containing recurring divalrt-net moieties derived from such dihydroxy arylhydrazones which exhibit second and/or third order nonlinear optical activity following external field orientation.

In one embodiment, the invention is a nonlinear optical material comprising dihydroxy arylhydrazones exhibiting nonlinear optical properties, represented by the formula:

$$Ar-\underset{\underset{R}{|}}{N}-N=\underset{\underset{A}{|}}{C}-A$$

wherein Ar is an aromatic hydrocarbon or heterocyclic radical, substituted with at least one electron withdrawing group, and containing up to 30 non-hydrogen atoms; A is independently at each occurrence either R or a $C_{6-30}$ aromatic group, optionally substituted with one or more hydroxy groups; and R is hydrogen or a $C_1$ to $C_{20}$ hydrocarbyl radical: provided that there are at least two aromatically substituted hydroxy groups in the aryl hydrazone molecule.

In another embodiment, the invention is a nonlinear optical material exhibiting nonlinear optical properties, comprising at least one divalent moiety derived from a dihydroxy arylhydrazone exhibiting nonlinear properties, represented by the formula:

$$Ar-\underset{\underset{R}{|}}{N}-N=\underset{\underset{A}{|}}{C}-A$$

wherein Ar is an aromatic hydrocarbyl or heterocyclic radical, substituted with at least one electron withdrawing group, and containing up to 30 non-hydrogen atoms; A is independently at each occurrence either R or a $C_{6-30}$ aromatic group, optionally substituted with one or more hydroxy groups; and R is hydrogen or a $C_1$ to $C_{20}$ hydrocarbyl radical; provided that there are at least two aromatically substituted hydroxy groups in the aryl hydrazone molecule.

In still another embodiment, the invention is a polymeric composition exhibiting nonlinear optical properties, comprising recurring divalent backbone moieties derived from a dihydroxy arylhydrazone represented by the formula:

$$Ar-\underset{\underset{R}{|}}{N}-N=\underset{\underset{A}{|}}{C}-A$$

wherein Ar is an aromatic hydrocarbyl or heterocyclic radical, substituted with at least one electron withdrawing group, and containing up to 30 non-hydrogen atoms; A is independently at each occurrence either R or a $C_{6-30}$ aromatic group, optionally substituted with one or more hydroxy groups; and R is hydrogen or a $C_1$ to $C_{20}$ hydrocarbyl radical; provided that there are at least two aromatically substituted hydroxy groups in the aryl hydrazone molecule.

The nonlinear optical polymeric compositions of the present invention do not depend upon oriented dopant molecules or large pendent chromophores as do many prior art materials.

DETAILED DESCRIPTION OF THE INVENTION

Hydrazone containing materials useful for a number of applications other than the NLO applications of the instant invention are disclosed in U.S. Pat. Nos. 4,621,156 and 4,732,904. These patents are hereby incorporated by reference for their relevant teachings related to preparation of arylhydrazones.

Suitably, Ar is selected from a group consisting of:

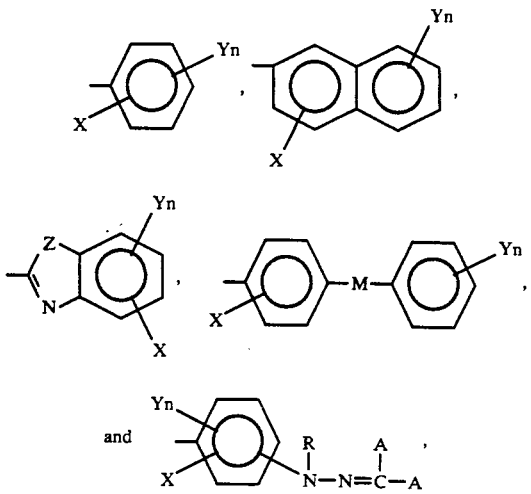

wherein X is either hydrogen or hydroxyl: Z is selected from a group consisting of O, S and NR; M is either a covalent bond or a divalent conjugated group; Y is an electron-withdrawing group: n is an integer from 1 to 4: and R is as defined hereinabove.

The term "electron withdrawing", as employed herein, refers to any substituent which attracts the electrons from a conjugated electron structure, thereby providing a polarized resonating structure. A quantification of the level of electron-withdrawing capability is given by the Hammett $\sigma$ (sigma) constant. This well known constant is described in many references, for instance, J. March *Advanced Organic Chemistry* (McGraw Hill Book Company, NY, 1977 edition) p. 251-259. The Hammett constant values are negative for electron donating groups ($\sigma_p = -0.66$ for $NH_2$) and positive for electron withdrawing groups ($\sigma_p = 0.78$ for a nitro group, op indicating para substitution.)

Preferred electron withdrawing groups are those having a Hammett constant ($\sigma_p$) of at least 0.50, and more preferably at least 0.60.

Illustrative of the electron withdrawing groups useful in the present invention include $-NO_2$, $-SO_2R$, $-SO_2CH_2F$, $-SO_2CHF_2$, $-SO_2CF_3$, $-S(-NSO_2CF_3)CF_3$, $-CF_3$, $-CO_2R$, $-COCF_3$, $-CN$, cyanovinyl, dicyanovinyl, and tricyanovinyl, wherein R is as previously defined.

The term "conjugated" group, as employed herein refers to a moiety containing alternating double or triple bonds which facilitates the charge transfer character of the excited state and allows for large differences in the dipole moments of the ground and excited states. Conjugated moieties generally include groups which have, for example, a hydrocarbyl diradical comprising a single aromatic ring, multiple fused rings or multiple aromatic rings linked by carbon-carbon, carbon-nitrogen, or nitrogen-nitrogen double bonds. The conjugated groups may be substituted with pendant radicals such as alkyl, aryl, cyano, halo and nitro groups.

Illustrative divalent conjugated groups represented by M in the instant invention, include: $-C=C-$, $-CR=CR-$, $-CR=CR-CR=CR-$, $-CR=N-$, $-N=CR-$, and $-N=N-$, wherein R is as defined hereinbefore.

The term "aromatic hydroxy" refers to hydroxy groups that are directly attached to an aromatic ring.

Preferably, substituent A is selected from:

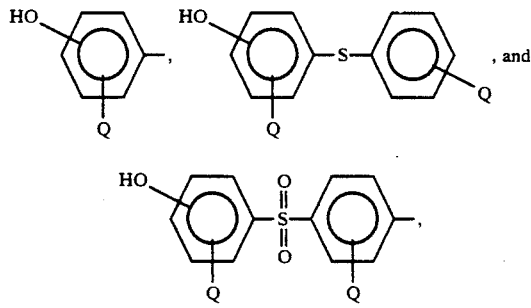

wherein Q is selected from a group consisting of hydrogen, hydroxyl, R, RO, RS, $R_2N$,

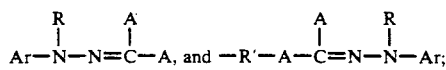

where A, R, and Ar are as previously defined, and R' is a divalent substituted or unsubstituted hydrocarbyl group containing 1 to 20 carbon atoms.

Arylhydrazones of the present invention are preferably dihydroxy arylhydrazones. More preferred hydrazones of the invention include derivatives of substituted hydroxybenzophenones, and hydroxybenzaldehydes. The most preferred hydrazones are those derived from 4,4'-dihydroxybenzophenone.

Dihydroxy arylhydrazones of the present invention can be suitably prepared by reaction of a hydrazine with a compound having one or more carbonyl groups, especially aldehydes or ketones.

Suitable hydrazines include those having the formula

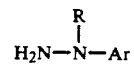

where R and Ar are as defined hereinabove.

Illustrative but not limiting examples of the hydrazines include 4-nitrophenylhydrazine, 2,4-dinitrophenylhydrazine, N'-methyl—N'-3-(hydroxy-4-nitrophenyl) hydrazine, N'-methyl—N'-4-(nitrophenylhydrazine), 6-nitro-2-benzothioazolylhydrazine, N'-methyl—N'[4-(p-hydroxyphenylsulfonyl)phenyl]hydrazine, 2,4-dinitro-1,5-bis($N^1$hydrazino)benzene, 2,4-bis(methylsulfonyl)-phenylhydrazine, 4-(methylsulfonyl)phenylhydrazine, and 4-(tricyanovinyl)phenylhydrazine. Preferred hydrazines useful for the present invention are substituted nitrophenylhydrazines.

Suitable carbonyl groups containing reactants for the purpose of this invention are of the general formula:

where A is independently at each occurrence as previously defined.

Illustrative but not limiting examples of such compounds are 4,4'-dihydroxybenzophenone, 4,4'-bis(4-hydroxyphenylthio)benzophenone, 4-hydroxybenzaldeyde, 3-hydroxy-4-methoxybenzaldehyde, 5,5'-methylene-bis-salicylaldehyde, 1,3-diacetylbenzene, 4,4'-bis(4-hydroxyphenylsulfonyl)benzophenone and 2,4-dihydroxy-benzaldehyde.

The hydrazones of the present invention can be provided by a suitably catalyzed reaction of a desired hydrazine compound with desired carbonyl containing reactants as are set forth hereinbefore. A catalyst such as a mineral acid or other acid is generally employed to increase the rate of the reaction. Acetic acid is suitably used as a catalyst and permits the convenient production of the desired hydrazone compounds. Preferably, the hydrazine compound is employed in an amount substantially equivalent with the available carbonyl content of the aldehyde or ketone. The reactants can be employed in a suitable solvent such a ethanol, methanol, m-xylene and such and brought to boiling. A catalyst such as acetic acid is added and additional solvent, where needed, can be added to obtain a solution of reactants. Upon cooling, the hydrazone is precipitated and recovered, as by filtration. The hydrazone recovered upon cooling can be recrystallized from a suitable solvent such as ethanol, ethanol-water mixture and the like.

The dihydroxy arylhydrazones of the invention exhibit nonlinear optical properties when subjected to a suitable poling force such as an electric field. Electric Field Induced Second-Harmonic Generation (EFISH(G)) has been used to determine the dipole moment-hyperpolarizability product, $\mu\beta$, of the hydrazone molecule. The methodology used is described by B.F. Levine and C.G. Bethea, J. Chem. Phys. 63 (1975) 2666-2682, incorporated herein by reference.

The dihydroxy arylhydrazone of the present invention differs from other molecules with NLO activity in that it is an aromatic diol and is a suitable monomer for preparing polycarbonate, polyestercarbonate, poly(hydroxy ether), polyether, and other optically transparent polymers via standard condensation polymerization or other processes. It is incorporated as recurring divalent moieties, forming the backbone of the polymer, which exhibits nonlinear active properties when oriented by application of an electric field.

The incorporation of the NLO active structures into the polymer backbone has a number of advantages. High levels of NLO chromophore functionalization can be achieved without increasing the scattering losses of waveguides fabricated from the polymer. The addition of the groups which add to the NLO activity of the polymer do not plasticize the polymer and lower the polymer Tg. In fact, such modifications can raise the polymer Tg. Furthermore, the fact the NLO chromophore is inherent to the polymer backbone increases the orientational stability of the NLO ohromophores, reducing the temporal decay of the NLO activity with time. Thus, polymers containing this monomer have the advantage of high Tg and increased orientation stability when fabricated into a nonlinear optical film or other NLO article in comparison to other NLO polymers.

It should be noted that as used herein, the terms "polymer" and "polymerization" are generic, and include either or both of the more specific cases of "homo-and co-polymers" and "homo- and co-polymerization", respectively. It should also be noted that "copolymer" includes both binary or higher order copolymers.

The polymers of this invention, thus, may be homopolymers containing divalent moieties derived from the dihydroxy arylhydrazones in the backbone of the polymer, or copolymers having at least one other comonomer copolymerized therewith.

Suitable comonomers polymerizable with the arylhydrazones are bisphenol A, or substituted bisphenol A, 9,9-bis(4-hydroxyphenyl)fluorene, or a substituted derivative of 9,9-bis(4-hydroxyphenyl)fluorene, and the mixtures thereof. Most preferred comonomers are 9,9-bis(4-hydroxyphenyl)fluorene, tetrachlorobisphenol A, and bisphenol A, and the mixtures thereof.

The mole ratio of the comonomer to the arylhydrazone, to be employed, varies in range from 90:10 to 10:90. The preferred mole ratio is 50:50. In the instances where mixture of comonomers is used, the arylhydrazone typically comprises 0.5 mole fraction of the polymer molecule.

The polymers of the present invention may be randomized or alternate polymers. The term "randomized" as used herein, refers to the fact that the hydrazone moieties and the comonomers appear in a random arrangement along the backbone of the polymer. The term "alternate" as used herein refers to the fact that the hydrazone moieties and the comonomer appear alternately along the backbone of the polymer.

Typically the polymers may be represented by the formulas:

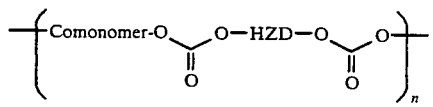

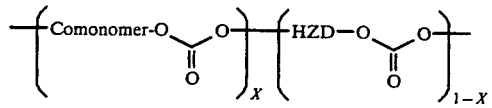

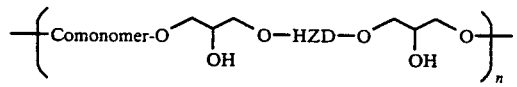

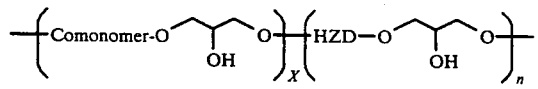

wherein HZD represents a divalent nucleus of aryl hydrazone, X is the mole fraction of the comonomer used and n is more than 1. The comonomers and hydrazone moieties are as described hereinbefore.

Methods of producing polycarbonates and polyestercarbonates are well-known in the prior art. Such method s are suitable for use in forming the polymeric compositions of the present invention.

Suitable methods for preparing polycarbonate resins are set forth in U.S. Pat. Nos. 3,248,414; 3,153,008: 3,215,668; 3,187,065; 3,028,365: 2,999,846; 2,964,974: 2,970,137; 1,991,273: and 2,999,835: all of which are incorporated herein by reference. The polycarbonates of the present invention are prepared by the reaction of the dihydroxyaryl hydrazones with a carbonate precursor. The carbonate precursor may be either a carbonyl halide, a diaryl carbonate or a bishaloformate. The carbonyl halides include carbonyl bromide, carbonyl chloride and mixtures thereof.

Similarly, methods of producing polyester-carbonates are known in the prior art. Exemplary of methods by which polyestercarbonates may be produced are those methods described in U.S. Pat. Nos. 3,169,121; 4,287,787: 4,156,069: 4,260,731: 4,330,662: 4,360,656: 4,374,973: 4,255,556: 4,388,455: 4,355,150; 4,194,038: 4,238,596: 4,238,597: 4,252,939: 4,369,303: and 4,105,633; and articles by Kolesnikov et al. published in Vysokomol Soedin as B9, 49 (1967): A9, 1012 (1967); A9, 1520 (1967): and A10, 145 (1968): all of which are incorporated herein by reference. Generally, the aforementioned processes involve the reaction of dihydroxyl containing compounds with phosgene or other suitable carbonate precursor or with a mixture phosgene or other carbonate precursor and a dicarboxylic acid, acid anhydride or acid halide.

Methods of producing poly(hydroxy ethers) and polyethers are well known in the prior art and are suitable for use in forming the polymeric compositions of the present invention. Suitable methods for preparing poly(hydroxy ethers) are set forth in U.S. Pat. Nos. 2,602,075; 3,305,528; 4,647,648; and 5,089,588: in articles by Reinking, Barnabeo, and Hale published in J. Appl. Polym. Sci., 7, 2135-2160 (1963): and in the Encyclopedia of Polymer Science and Technology, vol 10, 111-122 all of which are incorporated herein by reference.

Methods of fabricating films of NLO polymers and the methods of characterization of NLO activity are well known to those skilled in the art. Polymer films are typically fabricated by spin-coating or dip-coating a polymer solution onto a substrate. The substrate used depends on the poling method and method of characterization. For corona poling, a glass substrate such as a microscope slide is typically used. For parallel plate poling, a substrate with an electrically conductive surface is necessary, such as indium-tin-oxide (ITO) coated glass. The coated glass slides can be used directly for corona poling. The coated ITO slides for parallel plate poling require an electrically conductive overlayer, such as sputter-coated gold.

The fabricated NLO film must have a non-centrosymmetric alignment of the dipolar segments throughout the bulk of the polymer film. This is achieved by poling the film, or applying an electric field across the film. In corona poling, the field results form a discharge between a wire, such as tungsten, suspended above the film and a grounded heater block. The corona poling techinque is described further by M.A. Mortazavi, et al., J. Opt. Soc. Am. B 6 (1989). In paralled plate poling a voltage is applied across the two electrode layers. In both procedures a voltage is applied at elevated temperatures, near the polymer Tg (approximately 5°–10° C. above the onset of Tg as measured by DSC). The field is left on for at least a few minutes and the sample cooled with the field on to maintain the orientation of the dipolar segments.

The oriented film fabricated from the polymers of this invention can be characterized for their NLO activity by a Maker Fringe Rotation Second Harmonic Generation Technique which is well known to those skilled in the art. See for example, Singer et al., Appl. Phys. Lett. 49. (1986) 248-250.

The following preferred specific embodiments are to be construed as merely illustrative, and not limitative of the remainder of the disclosure in any way whatsoever. In the following examples, all temperatures are set forth uncorrected in degree Celsius; unless otherwise indicated, all parts and percentages are by weight.

EXAMPLE 1

4-Nitrophenylhydrazone of 4,4'-dihydroxybenzophenone [HZD-1]

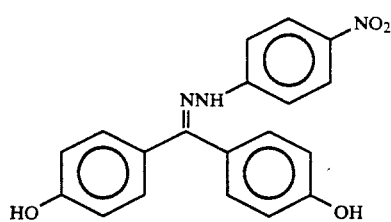

4,4'-Dihydroxybenzophenone (72.1 9), m-xylene (700 mL), 4-nitrophenylhydrazine (10.0 9, 10% water), and toluenesulfonic acid monohydrate (3.0 g) were heated to 140° C. (reflux) and water was separated with a Dean-Stark trap. Another 50.1 g of nitrophenylhydrazine (total 1.05 eq) was added in portions to control boiling due to the rapid evolution of water. After 7 h of heating, the reaction was allowed to cool to room temperature overnight, and the resulting solid collected by suction filtration. This solid was dissolved in 330 mL of hot 95% ethanol, filtered, and 120 mL of water was then gradually added. After cooling to room temperature, the orange-red solid was collected by suction filtration and dried at 95° C. in vacuo. Yield 105.8 g (90%), mp 245°–247° C.; $^1$H NMR (300 MHz, acetone-$d_6$) δ 9.14 (s, 1H), 8.85 (s, 1H), 8.65 (s, 1H), 8.11 (d, J=9 Hz, 2H), 7.48 (dd, J=2 and 9 Hz, 2H), 7.32 (d, J =9 Hz, 2H), 7.18 (dd, J=2 and 9 Hz, 2H), 7.04 (dd, J =2 and 9 Hz, 2 H), 6.85 (dd, J=2 and 9 Hz, 2H); $^{13}$C NMR (75 MHz, acetone-$d_6$) δ 159.3, 159.1, 151.8, 150.3, 140.2, 131.4, 131.0, 129.6, 126.5, 124.5, 117.2, 116.0, 112.7.

EXAMPLE 2

2,4-Dinitrophenylhydrazone of 4,4'-bis(4-hydroxyphenylthio)benzophenone [HZD-2]

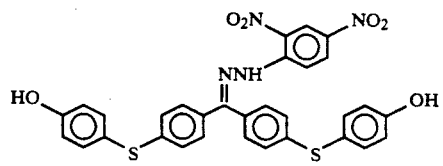

Preparation of 4,4'-bis(4-hydroxyphenylthio)benzophenone

A mixture of 4-mercaptophenol (50g, 0.317 mol for 80% purity), anhydrous potassium carbonate (46.9 9, g. 0.34 mol) and 150 mL of DMF was stirred and heated under nitrogen at 110°–120° C. for 90 min. The mixture was cooled to 80° C., a suspension of 4,4'-dichloro-benzophenone (40.1 g, 0.16 mol) in 100 mL DMF was added over 5 min and the mixture was stirred and heated under reflux for 4 h. After cooling to room temperature, there was added 400 mL of water and enough conc. HCl to adjust the pH to ca. 2. After stirring for 1 h, the pale yellow solid was filtered, washed with water and recrystallized from aqueous ethanol to afford 4,4'-bis(4-hydroxyphenylthio)benzo-phenone as pale yellow microcrystals, 59 g (86% yield), mp 219°–221° C. $^1$H NMR (DMSO-$d_6$) was consistent with the structure with a sharp singlet for OH at δ 10.02 and four sets of doublets for the aromatic protons ranging from δ 7.61 to 6.99.

Preparation of 2,4-Dinitrophenylhydrazone of 4,4'-bis(4-hydroxyphenylthio)benzophenone [HZD-2]

A mixture of 4,4'-bis(4-hydroxyphenylthio)-benzophenone (12.9 g, 30 mmol) from above, 2,4-dinitrophenylhydrazine (9 g, 46 mmol), ethanol (40 mL), and acetic acid (2 mL) was stirred and heated under reflux for 16 h. After cooling to room temperature, the orange solid was collected by filtration and identified as unreacted, excess 2,4-dinitrophenylhydrazine (2.7 g). The filtrate was evaporated and the residue was triturated with toluene to afford the title compound as orange crystals (17 g, 92%), mp 183°–185° C. Traces of 2,4-dinitrophenylhydrazine were removed by slurrying the crude product with 4N aqueous HCl and washing with water to yield a product with mp 195°–197° C. $^1$H NMR (DMSO-$d_6$) δ 11.10 (s, 1H, NH), 9.97 (s, 2H, OH), 8.80 (d, 1H, J=1.9 Hz), 8.40 (dd, 1H, $J_o$=8.2 Hz, $J_m$=1.9 Hz), 8.18 (d, 1H, $J_o$=8.2 Hz), and 7.6–6.8 (m, 16H).

EXAMPLE 3

N'-Methyl—N'-(3-hydroxy-4-nitrophenyl)hydrazone of 4-hydroxybenzaldehyde [HZD-3]

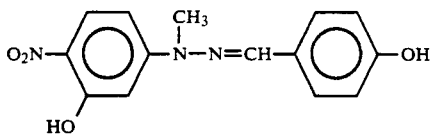

A mixture of 36.3 g (0.12 mol) of N'-methyl—N'-(3-methoxy-4-nitrophenyl)hydrazone of 4-hydroxy-benzaldehyde, prepared by heating the hydrazine and the carbonyl components together in ethanol with acetic acid as catalyst for 3 hrs as described in previous examples, and 300 mL of 2,4,6-collidine was stirred under nitrogen and 49 g of LiI was added. DMF (100 mL) was added to facilitate stirring and the mixture was heated at 125°–130° C. for 1 h. After cooling, 800 mL of cold water and 220 mL of conc. HCl were added slowly and the orange solid was filtered and recrystallized from acetone to provide the title compound as orange crystals (27 g, 79%), mp 170°–172° C.; $^1$H NMR (DMSO-d$_6$); δ 10.98 (s, 1H, OH), 9.95 (br s, 1H, OH), 7.94 (d, 2H, J=8.9Hz), 7.8 (m, 3H), and 7.00 (m, 3H).

EXAMPLE 4

N'-Methyl—N'-(3-hydroxy-4-nitrophenyl)hydrazone of 3-hydroxy-4-methoxybenzaldehyde [HZD-4]

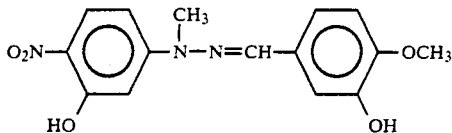

A mixture of N'-methyl-3-hydroxy-4-nitro-phenylhydrazine (12 9, 65 mmol), 3-hydroxy-4-methoxy-benzaldehyde (10.6 g, 70 mmol), ethanol (100 mL) and acetic acid (10 mL) was stirred and heated under reflux for 2 h. After cooling, the brick-colored precipitate was filtered, washed with ethanol and dried to give 14.7 g (69%) of the title compound; mp 216°–218° C.; $^1$H NMR (DMSO-d$_6$) δ 10.95 (br s, OH, 1 H), 9.22 (s, OH, 1H), 7.97 (dd, 1H, J$_1$=9.2 Hz, J$_2$=1.4 Hz), 7.88 (br s, 1H, CH=), 7.34 (br s, 1H), 7.13 (d, 1H, J=8.3 Hz), 7.07 (d,1H, J=8.3 Hz), 6.98 (m, 2H), 3.83 (s, 3H, OMe), and 3.38 (s, 3H, NMe).

EXAMPLE 5

4—Nitrophenylhydrazone of 4,4'-bis(4-hydroxyphenyl-thio)benzophenone [HZD 5]

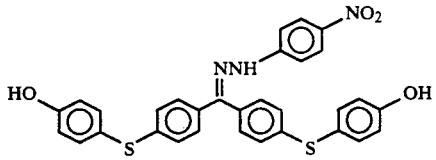

A 0.25 M solution of 4-nitrophenylhydrazine was prepared as follows: 16.6 g of 4-nitrophenylhydrazine (10% water) was heated at 80° C. with 233 g of concentrated phosphoric acid (85%) until dissolved. After dilution with 154 mL of ethanol (95%) and filtration through a thin pad of Celite, 385 mL of a dark orange solution was obtained.

A mixture of 4.00 g of bis[4-(4-hydroxy-phenylthio)]-benzophenone in 80 mL of ethanol was treated with the 4-nitrophenylhydrazine solution from above. After stirring for three days at room temperature, it was heated at 50° C. for 1 day and then poured into 400 mL of water. The aqueous layer was decanted from a red gummy precipitate. This gum was allowed to stand for two days with 200 mL of water and it solidified. It was collected and air dried to give 5.53 g. This material was combined with that from another run, based on 1.00 g of ketone, and recrystallized from ethyl acetate, giving 4.1 g of orange solid, mp 178°–80° C. A second crop yielded 0.6 g, for a total yield of 4.7 g (72%); $^1$H NMR (300 MHz, acetone-d$_6$) δ 9.41 (s, 1 H), 8.90 (br s, 2 H), 8.10 (d, J=9.4 Hz, 2 H), 7,48 (d, J=8.7 Hz, 2 H), 7.45 (d, J=8.6 Hz, 2 H), 7.39 (d, J=8.7 Hz, 2 H), 7.32 (d, J=9.1 Hz, 2 H), 7.22 (s, 4 H), 7.07 (d, J =8.6 Hz, 2 H), 7.00 (d, J=8.5 Hz, 2 H), 6.94 (d, J =8.7 Hz, 2 H); $^{13}$C NMR (75 MHz, acetone-d$_6$) δ 160.33, 159 94, 152.10, 148.88, 143.14, 142.04, 141.11, 138.42, 137.75, 136.79, 131.07, 130.38, 128.77, 128.15, 127.96, 126.88, 122.42, 121.16, 118.29, 118.07, 113.48.

EXAMPLE 6

Bis(4-nitrophenylhydrazone) of 5,5'-methylene-bis-salicylaldehyde

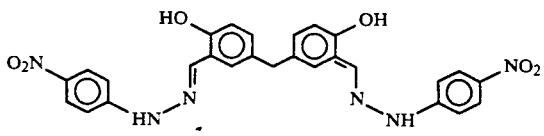

A stirred mixture of 5,5'-methylene-bis-salicylaldehyde (5.12 g, 20 mmol), ethanol (50 mL), 4-nitrophenylhydrazine (7.2 g, 42 mmol, 90%) and 10 mL of acetic acid was heated under reflux for 1 hr. and cooled. The yellow-orange precipitate was filtered, washed with ethanol and dried to provide 10.5 g (100%) of the title compound, mp >300° C.; $^1$H NMR (DMSO-d$_6$) δ 11.29 (s, 2H, NH), 10.01 (s, 2H, OH), 8.36 (s, 2H, CH=), 8.12 (d, 4H, J=9.3 Hz), 7.64 (d, 2H, J=2 Hz), 7.10 (m, 6H), 6.86 (d, 2H, J=8.3 Hz), and 3.86 (s, 2H, CH$_2$).

EXAMPLE 7

Bis(N'-methyl-4-nitrophenylhydrazone) of 5,5'-methylene-bis-salicylaldehyde [HZD-6B]

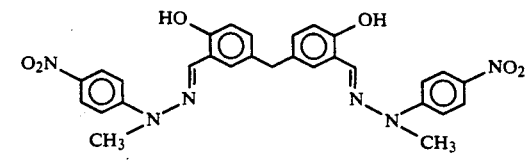

The title compound was prepared by reacting N'-methyl-4-nitrophenyl hydrazine with 5,5'-methylene-bis-salicylaldehyde as described for HZD-6A. The product was obtained as a yellow (slight orange hue) amorphous powder in 93.8% yield; mp 191°–193° C.; $^1$H NMR (DMSO-d$_6$) δ 10.07 (br s, OH, 2H), 8.15 (s, 2H, CH=), 8.12 (d, 4H, J =9.4 Hz), 7.64 (d, 2H, J=1.8 Hz), 7.44 (d, 4H, J =9.4 Hz), 7.11 (dd, Jl=8.3 Hz; J2=1.8 Hz, 2 H), 6.90 (d, 2H, J=8.3 Hz), 3.90 (s, 2H, CH$_2$), and 3.52 (s, 6H, NMe).

EXAMPLE 8

Bis[N'-methyl—N'-(3-hydroxy-4-nitrophenyl)hydrazone] of 1,3-diacetylbenzene [HZD-7]

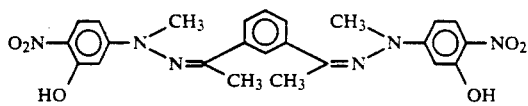

To a stirred mixture of N'-methyl-3-hydroxy-4-nitrophenylhydrazine (4 9, 22 mmol) and ethanol (40mL) was added 1,3-diacetylbenzene (1.62 9, 10 mmol) and 5 mL of acetic acid. The mixture was stirred and heated under reflux for 3 h and cooled. The dark yellow solid was filtered and recrystallized from DMF-ethanol to yield the title compound as yellow crystals (3.7 g, 75%); mp 164°-166° C.; $^1$H NMR (DMSO-$d_6$) δ 10.95 (br s, 2H, OH), 8.45 (t, 1H, J=1.8 Hz), 8.11 (dd, 2H, $J_1$=8.2 Hz, $J_2$ =1.8 Hz), 7.94 (d, 2H, J=9.6 Hz), 7.64 (t, 1H, J=8.2 Hz), 6.58 (dd, 2H, $J_1$=9.6 Hz, $J_2$=2.5 Hz), 6.39 (d, 1H, J =2.5 Hz), 3.33 (s, 6H, NMe), and 2.45 (s, 6H, CMe).

EXAMPLE 9

4-Nitrophenylhydrazone of 4,4'-bis(4-hydroxybenzenesulfonyl)benzophenone [HZD-8]

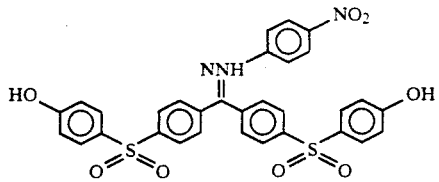

To a stirred mixture of 4,4'-bis(4-hydroxybenzenesulfonyl)benzophenone (4.94 9, 10 mmol) and ethanol (45 mL) was added 4-nitrophenylhydrazine (1.68 g, 10 mmol, 90%) and 10 mL of acetic acid. The mixture was stirred and heated under reflux for 15 min, cooled, and the yellow precipitate was filtered and washed with ethanol. After drying in vacuo at 100° C. for 6 h, the title compound was obtained as an amorphous yellow powder (5.7 g, 90.6%); mp 265°-268° C.; $^1$H NMR (DMSO-$d_6$) δ 10.70 ( br s, 2H, OH), 10.26 (s, 1H, NH), 8.11 (dd, 4H), 7.87 (dd, t, 4H), 7.75 (d, 2H), 7.59 (m, 4H), 7.40 (d, 2H), 7.0 (d, 2H), 6.92 (d, 2H).

EXAMPLE 10

6-Nitro-2-benzothiazolylhydrazone of 4,4,-dihydroxybenzophenone

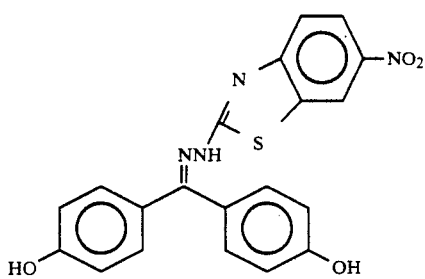

A mixture of 6-nitro-2-benzothiazolylhydrazine (10.5 g, 50 mmol), 4,4'-dihydroxy-benzophenone (10.1 g, 51 mmol), ethanol (50 mL), and 5 mL of conc. sulfuric acid was stirred and heated under reflux for 16 h. After cooling, the yellow precipitate was filtered, washed with ethanol, and dried to afford the title compound (18.2 g, 89%); mp 305°-307° C.; $^1$H NMR (DMSO-$d_6$) δ 11.90 (br s, NH), 9.86 (s, 1H, OH), 9.78 (s, 1H, OH), 8.7 (s, 1H), 8.15 (d, 1H, J=7.8 Hz), 7.4 (m, 3 H), 7.14 (d, 2H, J=9.0 Hz), 6.85 (d, 2H, J=9.0Hz), and 6.80 (d, 2H, J=9.0 Hz).

EXAMPLE 11

N'-Methyl—N,[4'-(p-hydroxyphenylsulfonyl-phenyl)-]hydrazone of 3-hydroxy-4-methoxybenzaldehyde [HZD-10]A mixture of N'-methyl- N'[4'-(p-hydroxyphenyl-

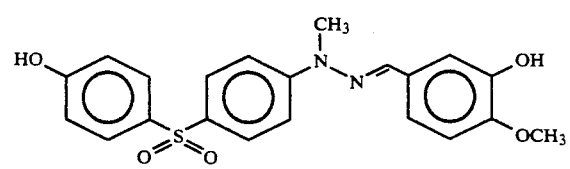

sulfonyl)]hydrazine (5.6 9, 20 mmol), ethanol (40 mL), 3-hydroxy-4-methoxybenzaldehyde (3.4 9, 22 mmol) and 2 ml of acetic acid was stirred and heated under reflux for 5 h. After cooling at room temperature for 3 h, the pale yellow solid was filtered and recrystallized from 120 mL of acetic acid to afford the title compound as pale yellow, shiny crystals (5.7 g, 71%), mp 211°-213° C.; 1H NMR (DMSO-$d_6$) δ 7.76 (s, 1H, CH=), 7.74 (m, 4H), 7.48 (d, 2H, J=7.2 Hz), 7.27 (d, 1H, J=2 Hz), 7.10 (dd, 1H, $J_1$=8.4 Hz, $J_2$ =2 Hz), 6.95(d, 1H, J=8.4 Hz), 6.90 (d, 2H, J=8.7 Hz), 3.80 (s, 3H, OMe), and 3.42 (s, HH, NMe).

EXAMPLE 12

2,4-Dinitro-1,5-bis(N2-4-hydroxybenzylidene-N1-hydrazino)benzene [HZD-11]

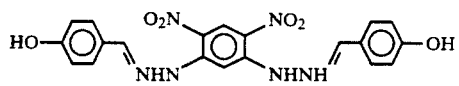

A mixture of 2,4-dinitro-1,5-dihydrazinobenzene (28 g, 118 mmol), 4-hydroxy-benzaldehyde (36.6 g, 300 mmol), 320 mL of nitrobenzene, and 6 mL of acetic acid was stirred and heated at 85°-90° C. for 3 h and stirred at room temperature for 16 h. Ethanol (500 mL) was added, the mixture was stirred at 60° C. for 15 min, and the orange solid was filtered and washed with ethanol. The material was purified by dissolving in 450 mL of DMSO, heating briefly to 130° C., and cooling the solution. The title compound was recovered as shiny orange crystals (31 g, 86.1%); mp 325° C. (dec); $^1$H NMR (DMSO-$d_6$) δ 11.28 (s, 2H, OH), 10.11 (s, 2H, NH), 8.95 (s, 1H), 8.53 (s, 2H), 8.13 (s,1H), 7.68 (d, 4H, J=8.6 Hz), and 6.96 (d, 4H, J=8.6 Hz). The NH and OH signals exchange with $D_2O$ a 60° C.

EXAMPLE 13

2,4-Bis(methylsulfonyl)phenylhydrazone of 4,4'-dihydroxybenzophenone [HZD-12]

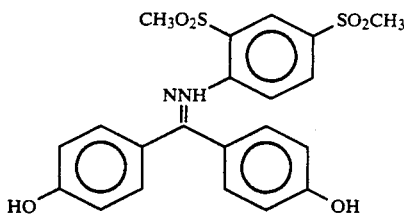

2,4-Bis(methylsulfonyl)phenylhydrazine (5.50 g, 1.0 eq) and phosphoric acid (1.0 g, 85%) were added to a solution of 4,4'-dihydroxybenzophenone (4.46 g) in 30 mL of absolute ethanol (2B) and heated at reflux for 18 h. The reaction mixture was poured into 50 mL of water with vigorous stirring. The resulting white solid precipitate was collected by suction filtration and air dried to give 9.3 g. Recrystallization from methanol afforded 8.2 g (75% yield) in two crops after vacuum drying. The two crops which were analytically equivalent were combined, mp 285°–286° C.; $^1$H NMR (300 MHz, acetone-d$_6$) δ 9.90 (s, 1 H), 8.9 (br s, 2 H), 8.16 (d, J = 2.0 Hz, 1 H), 8.12 (d, J=9.0 Hz, 1 H), 8.05 (dd, J = 2.0 and 9.0 Hz, 1 H), 7.54 (d, J=8.8 Hz, 2 H), 7.26 (d, J=8.6 Hz, 2 H), 7.10 (d, J=8.5 Hz, 2 H), 6.88 (d, J=8.8 Hz, 2 H), 3.13 (s, 3 H), 3.07 (s, 3 H); $^{13}$C NMR (75 MHz, acetone-d$_6$) δ 159.82, 159.45, 153.56, 147.52, 134.66, 131.03, 130.90, 130.57, 130.16, 129.98, 124.10, 121.21, 117.36, 116.08, 115.54, 44.68, 43.33.

EXAMPLE 14

4-(Methylsulfonyl)phenylhydrazone of 4,4'-dihydroxybenzophenone [HZD-13]

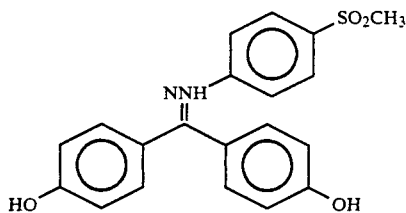

The general procedure used for the preparation of HZD-12 was followed. The resulting hydrazone was recrystallized from absolute ethanol (2B) and to afford 8.35 g (75% yield) of off-white fluffy solid, mp 271°–272° C.; $^1$H-NMR (300 MHz, acetone-d$_6$) δ 8.88 (s, 1 H), 8.8 (br s, 2 H), 7.72 (d, J=9.1 Hz, 2 H), 7.46 (d, J=8.7 Hz, 2 H), 7.36 (d, J=8.9 Hz, 2 H), 7.17 (d, J=8.6 Hz, 2 H), 7.03 (d, J=8.6, 2 H), 6.84 (d, J=8.8 Hz, 2 H), 3.02 (s, 3 H); $^{13}$C NMR (75 MHz, acetone-d6) δ 158.98, 158.93, 150.58, 148.60, 131.34, 131.24, 130.94, 129.70, 129.27, 124.61, 117.14, 115.87, 113.05, 44.92.

EXAMPLE 15

4-Nitrophenylhydrazone of 2,4-dihydroxybenzaldehyde [HZD-14]

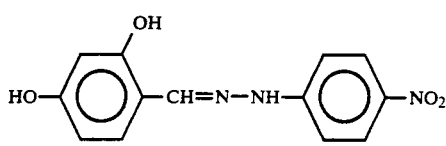

A solution of 64.3 g of 4-nitrophenylhydrazine in 1 L of conc. phosphoric acid was prepared with heating at 80°–90° C., diluted with 660 mL of 95% ethanol (2B), and filtered through a pad of filter-aid. To a solution of 49.7 g of 2,4-dihydroxybenzaldehyde in 150 mL of 95% ethanol was added 1.53 L of the 0.25 M 4-nitrophenylhydrazine solution prepared above. After stirring for 45 min at ambient temperature the reaction mixture was poured into 2 L of water. The resulting red solid was collected by suction filtration and air-dried, yielding 105.7 g. A 19.1 g sample was dissolved in 2 L of boiling acetone, which was then concentrated to 400 mL and cooled at room temperature overnight. After suction filtration and vacuum drying at 70° C. for 2h, 13.7 g was obtained, mp 280° C. (dec); $^1$H NMR (DMSO-d$_6$) δ 11.14 (s, 1H), 10.22 (s, 1H), 9.83 (s, 1H), 8.27 (s, 1H), 8.13 (d, J=9.3 Hz, 2 H), 7.52 (d, J=9.1 Hz, 1 H), 7.04 (d, J=8.9 Hz, 2 H), 6.37–6.34 (m, 2 H); $^{13}$C NMR (DMSO-d$_6$) δ 160.53, 158.16, 150.74, 141.96, 137.99, 128.58, 126.58, 112.09, 110.80, 108.11, 102.63.

EXAMPLE 16

4-(Tricyanovinyl)phenylhydrazone of 4,4'-dihydroxybenzophenone [HZD-15]

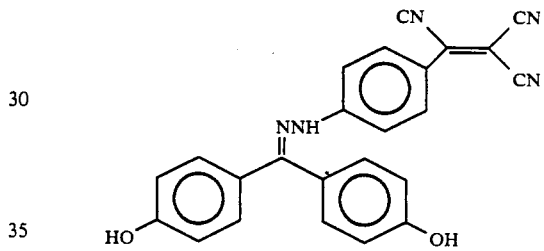

To a solution of 21.4 g of 4,4'-dihydroxy-benzophenone in 100 mL of absolute ethanol was added 15.0 g of phenylhydrazine (1.4 eq) and 6 drops of concentrated sulfuric acid. The mixture was heated at reflux for 22 h and then 150 mL of water was added while hot. Crystallization occurred upon cooling to 25° C. The phenylhydrazone of 4,4'-dihydroxybenzophenone was collected by suction filtration and air dried to give 25.8 g, mp 191°–193° C.

Tetracyanoethylene (8.7 g, 1.00 eq) was added to a solution of 20.7 g of the phenylhydrazone of 4,4'-dihydroxybenzophenone in 100 mL of DMF at 25° C., stirred for 43 h, and then poured into 350 mL of vigorously stirred water. The resulting blue-black precipitate was collected by suction filtration, air dried, and recrystallized from 300 mL of methanol (cooling to 0° C.). The yield of the title compound after vacuum drying at 50° C. for 3 h was 22.45 g (81%), mp 250°–251° C.; $^1$H NMR (300 MHz, acetone-d$_6$)δ 9.8 (br s, 1 H), 9.0 (br s, 2 H), 8.05 (d, J=9.9 Hz, 2 H), 7.51 (d, J =8.7 Hz, 2 H), 7.45 (br s, 2 H), 7.20 (d, J=8.6 Hz, 2 H), 7.04 (d, J=8.6, 2 H), 6.87 (d, J=8.8 Hz, 2 H); $^{13}$C NMR (75 MHz, acetone-d$_6$) δ 160.48, 159.90, 153.82, 153.17, 138.86, 133.90, 131.95, 130.89, 130.57, 124.43, 121.10, 117.59, 116.44, 115.84, 115.12, 114.78 (br), 80.5.

EXAMPLE 17

2,4-Dinitrophenylhydrazone of 4,4'-dihydroxybenzophenone [HZD-16]

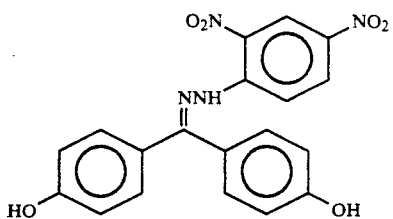

A solution of 4,4′dihydroxybenzophenone (22.7 g) and 110 mL of absolute ethanol was heated to 80° C. and 2,4-dinitrophenylhydrazine (30.0 g, 30% water) and 2 mL of concentrated phosphoric acid were added. After heating 19 h, the red solution was cooled to 25° C. and the resulting red precipitate was collected by suction filtration. The solid was dissolved in ethyl acetate and filtered to remove some undissolved material. Three recrystallizations from ethanol afforded 19.3 g of brick-red solid, mp 271°–273° C.; $^1$H-NMR (300 MHz, DMSO-$d_6$) δ 11.14 (s, 1H), 10.03 (br s, 2 H), 8.80 (d, J=2.5 Hz, 1 H), 8.38 (dd, J=2.5 and 9.6 Hz, 1 H), 8.14 (d, J=9.8 Hz, 1 H), 7.49 (d, J=8.5 Hz, 2 H), 7.23 (d, J=8.2 Hz, 2 H), 7.02 (d, J=8.1 Hz, 2 H), 6.82 (d, J=8.6 Hz, 2 H).

EXAMPLE 18

Measurement of the NLO activity of the Hydrazone Diols

The second-order NLO activities of the hydrazone diols of Examples 1–3, 5–6, 8–13, and 15 were determined in solution using the Electric Field Induced Second Harmonic Generation (EFISH) technique (see B. F. Levine and C. G. Bethea, J. Chem. Phys., 63, 2666, 1975). A pulsed voltage of 5 KV was applied to electrodes in a solution cell with 2mm electrode separation. The 5 KV pulses were synchronized with the firing of the laser (25 Hz). The input and output windows were sandwiched between the electrodes to achieve a wedge angle of 3.08° across the cell. The second harmonic generation (SHG) signal created by the solution was detected at a photomultiplier and was measured over a range of solution concentrations and normalized to the signal from a quartz reference wedge. The $\mu\beta$ product for the test molecule was determined from the SHG data as described by Levine and Bethea, supra. The excitation wavelength used was with 1064 nm from a QuantaRay DCR-2a Nd$_3$+/Yag laser, or 1579 nm by Raman shifting (in H$_2$ gas at 400 psi) the 532 nm frequency doubled (using a KDP crystal) output of the same laser. The results for the measurements of $\mu\beta$, conducted at 1064 nm fundamental excitation, are shown in Table I. These are among the highest $\mu\beta$ values reported to date. Also shown are the solvents that were used.

TABLE I

| Hydrazone Diol | $\mu\beta(10^{-48}$ esu) |
|---|---|
| HZD-1 | −827 (THF), 1200 (CH$_3$OH) |
| HZD-2 | −1,230 (THF) |
| HZD-3 | −656 (DMF) |
| HZD-5 | −859 (THF) |
| HZD-6A | 2,570 (DMF) |
| HZD-7 | 1,110 (DMF) |
| HZD-8 | 304 (THF) |
| HZD-9 | 604 (THF) |
| HZD-10 | 100 (DMF) |
| HZD-11 | −863 (DMF) |
| HZD-12 | 110 (DMF) |

TABLE I-continued

| Hydrazone Diol | $\mu\beta(10^{-48}$ esu) |
|---|---|
| HZD-13 | 115 (DMF) |
| HZD-15 | 2,441$^a$ (THF) |

$^a$Determined at 1579 nm.

EXAMPLE 19

This Example described the synthesis of an alternating copolycarbonate of bisphenol A (BA) and HZD-1. A 1 L 4-neck round bottom equipped with a thermometer, condenser, phosgene/nitrogen inlet, and a paddle stirrer connected to a Cole Parmer servodyne was charged with BA dischloroformate (25.25 g, 0.072 mol), HZD-1 (24.97 g, 0.072 mol), and CH$_2$Cl$_2$ (375 mL). The mixture was stirred at 250 rpm with a slow nitrogen purge and pyridine (18.1 g, 0.229 mol) was added over 13 min while maintaining the reaction temperature at 18°–28° C. Following the pyridine addition, 1.0 g phosgene was bubbled into the reaction mixture over 5 min, resulting in a viscous red-orange mixture. The reaction mixture was worked up by adding methanol (5 mL), a solution of 7 mL of conc. HCl in 50 mL water, and 100 mL of CH$_2$Cl$_2$. After stirring for 15 min at 200 rpm, the mixture was transferred to a separatory funnel. The CH$_2$Cl$_2$ layer was separated and washed with water (200 mL), a solution of 10 g NaHCO$_3$ in 150 mL water, water (200 mL), and then passed through a column of macroporous sulfonic acid ion exchange resin (300 mL bed volume). A portion of the copolycarbonate was isolated by adding part of the CH$_2$Cl$_2$ solution to 3 volumes of methanol in a high speed blender. The yellow precipitate was collected by suction filtration, dried in a hood overnight, and then dried for 48 h in a vacuum oven at 120° C. The resulting copolycarbonate had an inherent viscosity (IV) of 0.40 dL/g (determined in CH$_2$Cl$_2$ at 0.5 g/dL and 25° C.), and an extrapolated onset glass transition temperature (Tg) of 217° C. (determined by DSC at a scan rate of 20° C./min). $^1$H NMR (CDCl$_3$) and IR analyses were in agreement with the BA/HZD-1 monomer feed molar ratio of 50/50.

Preparation of a film of the polycarbonate

A film (1.32 $\mu$m thickness) was prepared by dip-coating using a CH$_2$Cl$_2$ solution of this copolycarbonate. The film was dried at 20° C. for 18 h in air, 100° C. for 2 h in air, 100° C. for 2 h under vacuum, and then at 200° C. for 18 h under vacuum. The film was corona poled with a maximum poling temperature of 211° C., applied voltage of 4 kV, and current of 3.0 microamps. After 30 min the sample was cooled to 20° C. while maintaining the electric field. The NLO activity coefficient d$_{33}$ was determined by second-harmonic generation measurements relative to a quartz reference crystal using the Maker Fringe rotation method (see K.D. Singer, et al., Appl. Phys. Lett., 49 248, 1986). A d$_{33}$ value of 21×10$^{-9}$ esu was determined for this electrically-oriented film sample.

EXAMPLE 20

The general synthetic procedure of Example 19, using BA bischloroformate, was followed to prepare an alternating copolycarbonate of BA and HZD-6A which had an IV of 0.17 dL/g (DMF, 0.5 g/dL, 25° C.) and a Tg of 175° C. A corona poled film of this copolycarbonate had a d$_{33}$ value of 28×10$^{-9}$ esu when prepared and measured according to the general procedure of Example 19.

EXAMPLE 21

This Example describes the synthesis of a random copolycarbonate of tetrachlorobisphenol A (TCBA) and HZD-1. A 500 mL round bottom equipped as in Example 19 was charged with TCBA (11.93 g, 0.033 mol), HZD-1 (11.38 g, 0.033 mol), pyridine (13.6 g, 0.172 mol), and $CH_2Cl_2$ (200 mL). The solution was stirred at 250 rpm and phosgene (7.5 g, 0.076 mol) was bubbled in over 15 min. The reaction mixture was worked up according to the general procedure of Example 18, resulting in 20.1 g of yellow copolycarbonate with an IV of 0.48 dL/g ($CH_2Cl_2$, 0.5 g/dL, 25° C.) and Tg >250° C. $^1$H NMR ($CDCl_3$) results were in agreement with a TCBA/HZD-1 molar ratio of 50/50. A film (2.28 mm thickness) was prepared by dip-coating using a $CH_2Cl_2$ solution of this copolycarbonate. The film was dried at 20° C. for 24 h in air and then at 100° C. for 18 h under vacuum. The film was corona poled with a maximum poling temperature of 248° C., applied voltage of 4 kV, and current of 3.5 microamps. After 20 min the sample was cooled to 20° C. while maintaining the electric field. The measured NLO activity coefficient $d_{33}$ was $9 \times 10^{-9}$ esu.

EXAMPLE 22

Additional random copolycarbonates were prepared according to the general procedure of Example 21 using hydrazxone diols, BA, and 9,9-bis(4-hydroxyphenyl)-fluorene (BHPF). Table II shows the compositions prepared and results for IV (determined in $CH_2Cl_2$), Tg, and $d_{33}$. The $d_{33}$ values were determined at 1064 nm fundamental excitation as described in Example 19. The samples were piled using either corona poling (CP) or parallel plate poling (PP) techniques.

TABLE II

| Monomers[a]   | IV (dL/g) | Tg (°C.) | $d_{33}$ ($10^{-9}$ esu) | Poling Type |
|---------------|-----------|----------|--------------------------|-------------|
| BA/HZD-2      | 0.25      | 183      | 20                       | CP          |
| BHPF/HZD-1    | 0.74      | >250     | NM[b]                    | —           |
| BA/HZD-3      | 0.34      | 191      | NM[b]                    | —           |
| BA/HZD-15     | 0.47      | 214      | 69[c]                    | PP (0.8)[d] |
| BA/HZD-4      | 0.26[e]   | 186      | NM[b]                    | —           |
| BA/HZD-5      | 0.14      | 166      | 25                       | CP          |
| BA/BHPF/HZD-1[f] | 0.28   | >250     | NM[b]                    | —           |
| BA/HZD-7      | 0.15      | 144      | NM[b]                    | —           |
| BA/HZD-1      | 0.22      | 193      | 27                       | PP (0.5)    |

[a]50/50 Molar ratio unless indicated otherwise.
[b]Not measured.
[c]Determined using 1579 nm excitation.
[d]Value in parentheses is electric field strength in MV/cm.
[e]Measured in DMF.
[f]25/25/50 Molar ratio.

EXAMPLE 23

This Example describes the synthesis of an alternating copoly(hydroxy ether) of BA and HZD-1. HZD-1 (10.48 g, 30.0 mmol, 60.0 meq wt phenol), BA diglycidyl ether (10.59 g, 61.20 meq wt epoxide, EEW=173.0 g /equiv wt epoxide), and propylene glycol monophenyl ether (13 mL) were added to a 100 mL polymerization reactor which was then fitted with a thermometer, overhead mechanical stirrer, and nitrogen inlet and outlet adapters. The mixture was heated to 140° C. and 15 drops of 70% ethyltriphenylphosphonium acetate in methanol were added. The temperature of the reaction mixture rose to 175° C. over 10-15 min and was maintained at 160°–165° C. for 30 min as the solution became increasingly viscous. Propylene glycol monophenyl ether (10 mL) was added when the solution reached maximum viscosity. The solution was stirred at 140°–145° C. for 20 min then diluted to a volume of 100 mL with DMF. The solution was precipitated into a solution of 3/1 methanol/water (400 mL). The product was washed with methanol (400 mL) and water (400mL) in a high speed blender. The orange powder was collected via filtration, air dried, and then redissolved in THF (100 mL). The polymer was precipitated a second time as described previously. After drying in vacuo at 80° C. for 24 h, 16.7 g of orange powder was obtained with an IV of 0.68 dL/g (DMF, 25.0° C.) and a Tg of 135° C. A corona poled film of this copoly(hydroxy ether) had a $d_{33}$ value of $21 \times 10^{-9}$ esu when prepared and measured according to the general procedure of Example 19.

EXAMPLE 24

The general procedure of Example 23 was used to prepare additional alternating copoly(hydroxy ethers) of BA and HZD-2, HZD-5, and HZD-6B. Table III shows the compositions prepared and results for IV (determined in DMF), Tg, and $d_{33}$. The $d_{33}$ values were determined at 1064 nm fundamental excitation as described in Example 19. The samples were poled using the corona poling technique.

TABLE III

| Monomers   | IV (dL/g) | Tg (°C.) | $d_{33}$ ($10^{-9}$ esu) |
|------------|-----------|----------|--------------------------|
| BA/HZD-2   | 0.18      | 130      | 29                       |
| BA/HZD-5   | 0.52      | 143      | 25                       |
| BA/HZD-6B  | 0.30      | 146      | 65                       |

EXAMPLE 25

This Example describes the synthesis of a random copoly(hydroxy ether) of BA and HZD-1. To a 100 mL polymerization kettle was added HZD-1 (8.73 g, 0.025 mol), BA (5.71g, 0.025 mol), ethanol (15 mL), epichlorohydrin (4.63 g, 0.050 mol), and sodium hydroxide (2.00 g, 0.050 mol) dissolved in water (10 mL). The flask was fitted with a top which contained a thermometer, an overhead mechanical stirrer, and a nitrogen inlet adapter. The contents of the flask were stirred at 25° C. under nitrogen for 16 h, then more sodium hydroxide (0.3 g, 0.0075 mol) in water (3 mL) was added to the reaction mixture. The contents of the flask were then heated at 80° C. for 0.5 h, after which time a dark, viscous polymeric mass formed. Chlorobenzene (5 mL) was added and then again after heating for 1h at 80° C. After heating for a total of 7h at 80° C., a dark, viscous polymeric mass precipitated. Phenol (1 g) in chlorobenzene (20 mL) was added and the mixture was heated for an additional 1.5 h. After cooling to 25° C., the nonpolymeric supernatant liquid was decanted. The polymeric mass was superficially washed with water several times and was dissolved in DMF (100 mL). The polymer was precipitated into 3/1 methanol/water (400 mL) in a high speed blender. The orange polymeric powder was collected via filtration, redissolved in THF (100 mL), and precipitated a second time into methanol. The polymer was collected via filtration and was washed with methanol (1 L) until the filtrate was colorless. After drying in vacuo at 80° C. for 24 h, 14.0 g of orange powder was obtained with an IV of 0.53 dL/g (DMF) and a Tg of 146° C. A corona poled film of this copoly(hydroxy ether) had a $d_{33}$ value of $34 \times 10^{-9}$ esu when prepared and measured according to the general procedure of Example 19.

EXAMPLE 26

The general procedure of Example 25 was used to prepare additional random copoly(hydroxy ethers) of BA and HZD-1, a random copoly(hydroxy ether) of BHPF and HZD-1, and the poly(hydroxy ether) of HZD-1. Table IV shows the compositions prepared and results for IV (determined in DMF), Tg, and $d_{33}$. The $d_{33}$ values were determined at 1064 nm fundamental excitation as described in Example 19. The samples were poled using the corona poling technique.

TABLE IV

| (Molar Ratio) | IV (dL/G) | Tg (°C.) | $d_{33}$ ($10^{-9}$ esu) |
| --- | --- | --- | --- |
| BA/HZD-1 (90/10) | 0.85 | 103 | 15 |
| BA/HZD-1 (75/25) | 0.33 | 116 | 24 |
| BA/HZD-1 (75/25) | 0.18 | 107 | 33 |
| BA/HZD-1 (25/75) | 0.38 | 167 | 19 |
| BHPF/HZD-1 (50/50) | 0.18 | 179 | 16 |
| HZD-1/HZD-1 | 0.27 | 177 | 17 |

EXAMPLE 27

The thermal stabilities of the poled films of the copolycarbonates of Examples 19 and 21 were evaluated by measuring the NLO activity coefficient $d_{33}$ following 100° C. exposure in a recirculating air oven. The results are shown in Table V.

TABLE V

| Monomers | Days at 100° C. | $d_{33}$ ($10^{-9}$ esu) |
| --- | --- | --- |
| BA/HZD-1 | 0 | 21 |
|  | 92 | 17 |
| TCBA/HZD-1 | 0 | 9 |
|  | 67 | 9 |

As evidenced by these results, the NLO compositions of this invention exhibit excellent stability of NLO activity following elevated temperature exposure.

What is claimed is:

1. A nonlinear optical material comprising dihydroxy arylhydrazones exhibiting nonlinear optical properties when oriented by an electric field, represented by the formula:

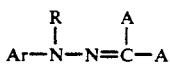

wherein Ar is an aromatic hydrocarbyl or heterocyclic radical, substituted with at least one electron withdrawing group, and containing up to 30 non-hydrogen atoms; A is independently at each occurrence either R or $C_{6-30}$ aromatic group, optionally substituted with one or more hydroxy groups; and R is hydrogen or a $C_1$ to $C_{20}$ hydrocarbyl radical; provided that there are at least two aromatically substituted hydroxy groups in the aryl hydrazone molecule.

2. The nonlinear optical material of claim 1, wherein Ar is selected from a group consisting of:

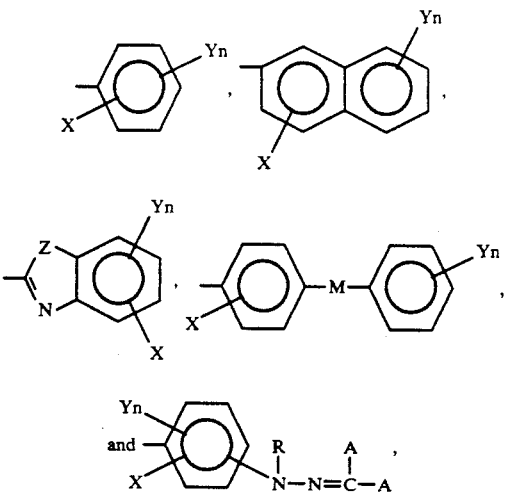

wherein X is either hydrogen or hydroxyl; Z is selected from a group consisting of O, S and NR; M is either a covalent bond or a divalent conjugated group: Y is an electron-withdrawing group: n is an integer from 1 to 4: and R is as defined hereinabove.

3. The nonlinear optical material of claim 2, wherein the divalent conjugated group is selected from a group consisting of —C=C—, —CR=CR—, —CR=CR—CR=CR—, —CR=N—, —N=CR—, and —N=N—, wherein R is as defined hereinabove.

4. The nonlinear optical material of claim 2, wherein Y is selected from the group consisting of $NO_2$, $SO_2R$, $SO_2CH_2F$, $SO_2CHF_2$, $SO_2CF_3$, $S(NSO_2CF_3)CF_3$, $CF_3$, $CO_2R$, $COCF_3$, cyano, cyanovinyl, dicyanovinyl, and tricyanovinyl, wherein R is a hydrogen or a $C_1$ to $C_{20}$ hydrocarbyl group.

5. The nonlinear optical material of claim 1, wherein A at each occurrence is independently selected from the group consisting of:

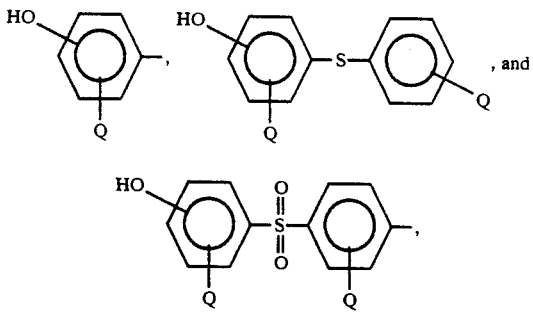

wherein Q is selected from a group consisting of hydrogen, hydroxyl, R, RO, RS, $R_2N$,

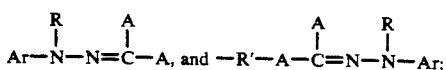

where A, R, and Ar are as previously defined, and R' is a divalent substituted or unsubstituted hydrocarbyl group containing 1 to 20 carbon atoms.

6. The nonlinear optical material of claim 1, wherein R is hydrogen, Ar is 4-nitrophenyl, and A at each occurrence is 4-hydroxyphenyl group.

7. The nonlinear optical material of claim 1, wherein R is hydrogen, Ar is 2,4-dinitrophenyl, and A at each occurrence is 4-hydroxyphenyl group.

8. The nonlinear optical material of claim 1, wherein R is hydrogen, Ar is 2,4-dinitrophenyl, and A at each occurrence is:

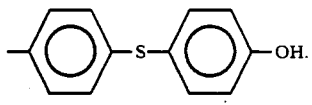

9. The nonlinear optical material of claim 1, wherein R is hydrogen, Ar is 4-nitrophenyl, A at each occurrence is

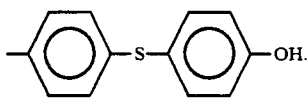

10. The nonlinear optical material of claim 1, wherein R is hydrogen, Ar is 4-nitrophenyl and A at each occurrence is

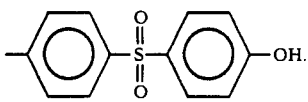

11. The nonlinear optical material of claim 1, wherein R is hydrogen, Ar is 4-methylsulfonylphenyl and A at each occurrence is 4-hydroxyphenyl.

12. The nonlinear optical material of claim 1, wherein R is hydrogen, Ar is 2,4-bis (methylsulfonyl)henylene and A at each occurrence is 4-hydroxyphenyl.

13. The nonlinear optical material of claim 1, wherein R is hydrogen, Ar is 4-ricyanovinylphenyl, and A at each occurrence is 4-hdroxyphenyl group.

14. The nonlinear optical material of claim 5, represented by the formula:

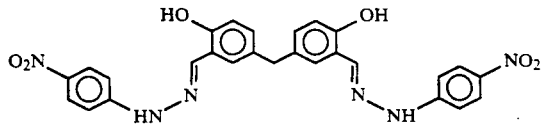

15. The nonlinear optical material of claim 5, represented by the formula:

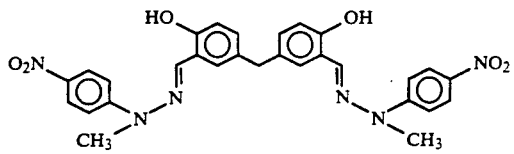

16. The nonlinear optical material of claim 5, represented by the formula:

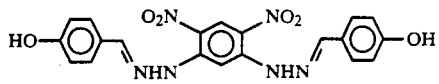

17. A nonlinear optical material comprising a composition containing a lest one divalent moiety derived from an aryl hydrazone exhibiting nonlinear optical properties when oriented by an electric field, the aryl hydrazone represented by the formula:

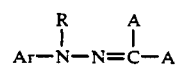

wherein Ar is an aromatic hydrocarbyl or heterocyclic radical, substituted with at least one electron withdrawing group, and containing up to 30 non-hydrogen atoms; A is independently at each occurrence either R or a $C_{6-30}$ aromatic group, optionally substituted with one or more hydroxy groups; and R is hydrogen or a $C_1$ to $C_{20}$ hydrocarbyl radical; provided that there are at least two aromatically substituted hydroxy groups in the aryl hydrazone molecule.

18. The nonlinear optical material of claim 17, wherein Ar is selected from a group consisting of:

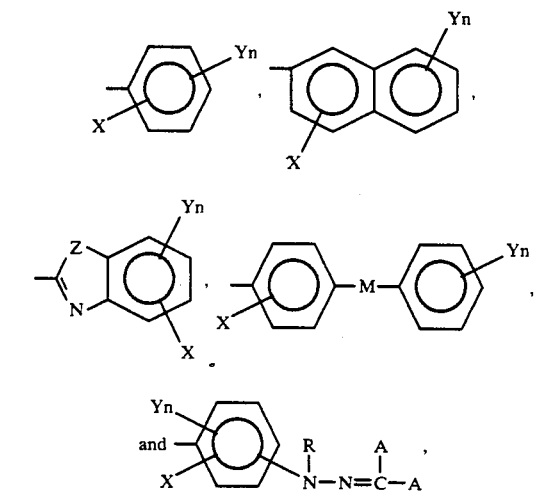

wherein X is either hydrogen or hydroxyl; Z is selected from a group consisting of O, S and NR, M is either a covalent bond or a divalent conjugated group: Y is an electron-withdrawing group: n is an integer from 1 to 4: and R is as defined hereinabove.

19. The nonlinear optical material of claim 18, wherein the divalent conjugated group is selected from a group consisting of —C≡C—, —CR=CR—, —CR=CR—CR=CR—, —CR=N—, —N=CR—, and —N=N—, wherein R is as defined hereinabove.

20. The nonlinear optical material of claim 18, wherein Y is selected from the group consisting of $NO_2$, $SO_2R$, $SO_2CH_2F$, $SO_2CHF_2$, $SO_2CF_3$, $S(NSO_2CF_3)CF_3$, $CF_3$, COR, $COCF_3$, cyano, cyanovinyl, dicyanovinyl, and tricyanovinyl, wherein R is a hydrogen or a $C_1$ to $C_{20}$ hydrocarbyl group.

21. The nonlinear optical material of claim 18, wherein A at each occurrence is independently selected from the group consisting of:

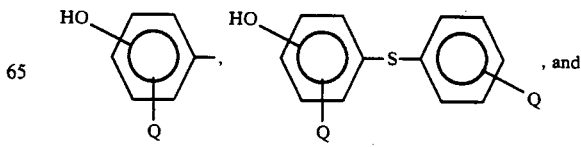

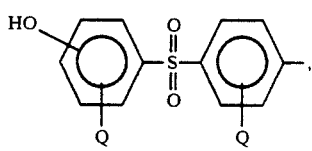

wherein Q is selected from a group consisting of hydrogen, hydroxyl, R, RO, RS, R₂N,

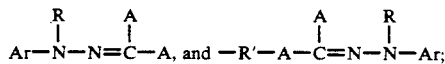

where A, R, and Ar are as defined hereinabove, and R' is a divalent substituted or unsubstituted hydrocarbyl group containing 1 to 20 carbon atoms.

22. The nonlinear optical material of claim 17, wherein R is hydrogen, Ar is 4-nitrophenyl, and A at each occurrence is 4-hydroxyphenyl group.

23. The nonlinear optical material of claim 17, wherein R is hydrogen, Ar is 2,4-dinitrophenyl, and A at each occurrence is 4-hydroxyphenyl group.

24. The nonlinear optical material of claim 17 wherein R is hydrogen, Ar is 2,4-dinitrophenyl, and A at each occurrence is:

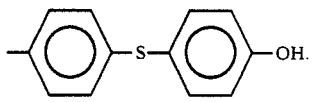

25. The nonlinear optical material of claim 17, wherein R is hydrogen, Ar is 4-nitrophenyl, A at each occurrence is

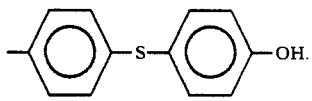

26. The nonlinear optical material of claim 17, wherein R is hydrogen, Ar is 4-nitrophenyl A at each occurrence is

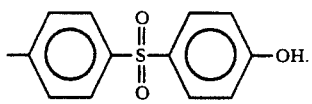

27. The nonlinear optical material of claim 17, wherein R is hydrogen, Ar is 4-methylsulfonylphenyl and A at each occurrence is 4-hydroxyphenyl.

28. The nonlinear optical material of claim 17, wherein R is hydrogen, Ar is 2,4-bis (methylsulfonyl)-phenylene and A at each occurrence is 4-hydroxyphenyl.

29. The nonlinear optical material of claim 17, wherein R is hydrogen, Ar is 4-tricyanovinyl phenyl, and A at each occurrence is 4-hydroxyphenyl group.

30. The nonlinear optical material of claim 21, represented by the formula:

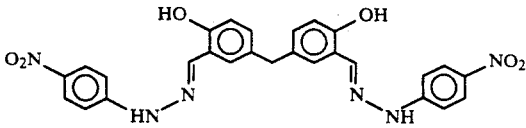

31. The nonlinear optical material of claim 21, represented by the formula:

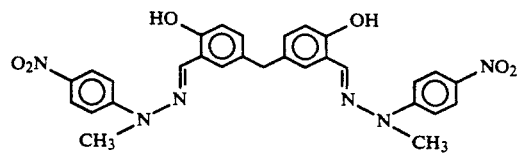

32. The nonlinear optical material of claim 21, represented by the formula:

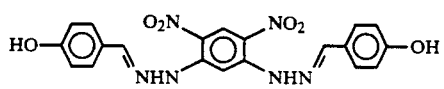

33. A nonlinear optical polymeric composition exhibiting nonlinear optical properties when oriented by an electric field comprising recurring divalent nuclei of a dihydroxy arylhydrazone in the backbone of the polymer, the aryl hydrazone being represented by the formula:

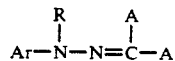

wherein Ar is an aromatic hydrocarbyl or heterocyclic radical, substituted with at least one electron withdrawing group, and containing up to 30 non-hydrogen atoms; A is independently at each occurrence either R or a $C_{6-30}$ aromatic group, optionally substituted with one or more hydroxy groups; and R is hydrogen or a $C_1$ to $C_{20}$ hydrocarbyl radical; provided that there are at least two aromatically substituted hydroxy groups in the aryl hydrazone molecule.

34. The nonlinear optical polymeric composition of claim 33 wherein the polymer is selected from the group consistent of polyester, polycarbonate, polyester-carbonate, polyether, and poly(hydroxy ether) polymers.

35. The nonlinear optical polymeric composition of claim 34, wherein Ar is selected from a group consisting of

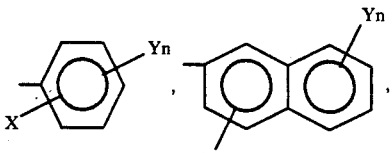

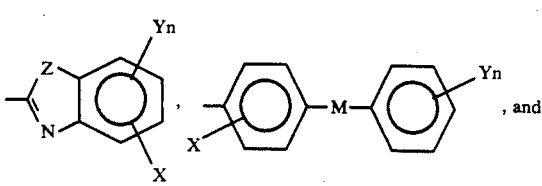

, and

-continued

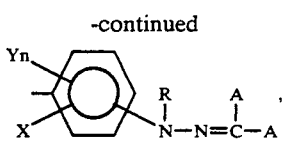

wherein X is either hydrogen or hydroxyl: Z is selected from a group consisting of O, S and NR: M is either a covalent bond or a divalent conjugated group: Y is an electron withdrawing group; n is an integer from 1 to 4; and R is as defined hereinabove.

36. The nonlinear optical polymeric composition of claim 35 wherein the conjugating group is selected from the group consisting of C≡C—, —CR=CR—, —CR=CR—CR=CR—, —CR=N—, —N=CR—, and —N=N—, wherein R is as defined hereinabove.

37. The nonlinear optical polymeric composition of claim 35, wherein Y is an electron-withdrawing group selected from a group consisting of $NO_2$, $SO_2R$, $SO_2CH_2F$, $SO_2CHF_2$, $SO_2CF_3$, $S(NSO_2CF_3)CF_3$, $CF_3$, COR, $COCF_3$, cyano, cyanovinyl, dicyanovinyl, and tricyanovinyl, wherein R is as defined hereinabove.

38. The nonlinear optical polymeric composition of claim 35 wherein A is independently selected each occurrence from a group consisting of

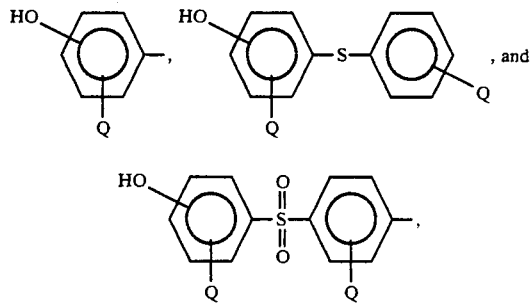

wherein Q is selected from a group consisting of hydrogen, hydroxyl, R, RO, RS, $R_2N$,

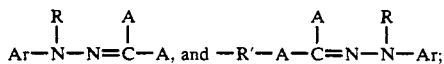

wherein A, R, and Ar are as defined hereinabove, and R' is a divalent substituted or unsubstituted hydrocarbyl group containing 1 to 20 carbon atoms.

39. The nonlinear optical polymeric composition of claim 38 wherein the polymer further comprises at least one other comonomer polymerizable therewith.

40. The nonlinear optical polymeric composition of claim 39 wherein at least one other comonomer is either a bisphenol A or a substituted bisphenol A.

41. The nonlinear optical polymeric composition of claim 39, wherein the aryl hydrazone is 4-nitrophenyl hydrazone of 4,4'-dihydroxybenzophenone.

42. The nonlinear optical polymeric composition of claim 40 wherein the polymer is a polycarbonate, comprising bisphenol A and 4-nitrophenyl hydrazone of 4,4'-dihydroxybenzophenone.

43. The nonlinear optical composition of claim 40 wherein the polymer is a polycarbonate comprising 4-tricyanovinyl hydrazone of 4,4'-dihydroxybenzophenone and bisphenol A.

44. The nonlinear optical polymeric composition of claim 41, wherein the polymer is a copolycarbonate comprising tetrachlorobisphenol A and 4-nitrophenyl hydrazone of 4,4'-dihydroxybenzophenone.

45. The nonlinear optical polymeric composition of claim 1 further comprising 9,9-bis(4-hydroxyphenyl)-fluorene, or a substituted derivative of 9,9-bis(4-hydroxphenyl)fluorene.

46. The nonlinear optical polymeric composition of claim 45 wherein the polymer is a polycarbonate comprising bisphenol A, 9,9-bis(4-hydroxyphenyl)fluorene and 4-nitrophenyl hydrazone of 4,4'-dihydroxybenzophenone.

47. The nonlinear optical polymeric composition of claim 39, wherein the polymer is a poly(hydroxy ether), comprising 9,9-bis(4-hydroxy-phenyl)fluorene and 4-nitrophenyl hydrazone of 4,4'-dihydroxybenzophenone.

48. The nonlinear optical polymeric composition of claim 39 wherein the polymer is a poly(hydroxy ether), comprising bisphenol A and 4-nitrophenylhdrazone of 4,4'-dihydroxybenzophenone.

49. The nonlinear optical polymeric composition of claim 39 wherein the polymer is a poly(hydroxy ether), comprising 9,9-bis(4-hydroxphenyl)fluorene and bis(N'-methyl-4-nitrophenylhydrazone) of 5,5'-methylene-bis-salicylaldehyde.

50. The nonlinear optical polymeric composition of claim 39 wherein the polymer is a poly(hydroxy ether), comprising bisphenol A and bis(N'-methyl-4-nitrophenylhydrazone) of 5,5'-methylene-bis-salicylaldehyde.

* * * * *

UNITED STATES PATENT AND TRADEMARK OFFICE
CERTIFICATE OF CORRECTION

PATENT NO. : 5,208,299

DATED : May 4, 1993

INVENTOR(S) : Stephen E. Bales; David J. Brennan; Robert J. Gulotty; Anthony P. Haag; Muthiah N. Inbasekaran It is certified that error appears in the above-identified patent and that said Letters Patent is hereby corrected as shown below:

On the Cover Page, the title of U.S. Patent 5,208,299 should correctly appear as --NOVEL NONLINEAR OPTICAL ARYLHYDRAZONES AND NONLINEAR OPTICAL POLYMERS THEREOF--;

Column 22, line 25, "group: n is an integer from 1 to 4:" should correctly appear as --group; n is an integer from 1 to 4;--;

Column 22, line 29, " -C=C- " should correctly appear as -- -C≡C- --;

Column 23, Claim 12, line 36, "(methylsulfonyl)henylene" should correctly appear as --(methylsulfonyl)phenylene--;

Column 23, Claim 13, line 39, "4-ricyanovinylphenyl" should correctly appear as --4-tricyanovinylphenyl--;

Column 23 Claim 17, line 68, "lest" should correctly appear as --least--;

Column 24, Claim 18, line 44, "group:" should correctly appear as --group;--;

Column 24, Claim 18, line 45, "group: n is an integer from 1 to 4:" should correctly appear as --group; n is an integer from 1 to 4;--

Column 27, Claim 35, line 8, "hydroxyl: Z" should correctly appear as --hydroxyl; Z--;

Column 27, Claim 35, line 9, "NR: M" should correctly appear as --NR; M--;

Column 27, Claim 35, line 10, "group: Y" should correctly appear as --group; Y--;

UNITED STATES PATENT AND TRADEMARK OFFICE
CERTIFICATE OF CORRECTION

PATENT NO. : 5,208,299

DATED : May 4, 1993

INVENTOR(S) : Stephen E. Bales; David J. Brennan; Robert J. Gulotty; Anthony P. Haag; Muthiah N. Inbasekaran It is certified that error appears in the above-indentified patent and that said Letters Patent is hereby corrected as shown below:

Column 28, Claim 45, line 23, "claim 1" should correctly appear as --claim 40--.

Signed and Sealed this

Twenty-fifth Day of January, 1994

*Attest:*

BRUCE LEHMAN

*Attesting Officer*     *Commissioner of Patents and Trademarks*